United States Patent [19]

Henrick et al.

[11] 4,359,424

[45] Nov. 16, 1982

[54] SUBSTITUTED PHENOXYETHOXYTETRAHYDROPYRAN

[75] Inventors: Clive A. Henrick; Gerardus B. Staal, both of Palo Alto, Calif.

[73] Assignee: Zoecon Corporation, Palo Alto, Calif.

[21] Appl. No.: 281,633

[22] Filed: Jul. 9, 1981

Related U.S. Application Data

[62] Division of Ser. No. 166,649, Jul. 7, 1980, Pat. No. 4,304,924.

[51] Int. Cl.$^3$ .......................................... C07D 309/12
[52] U.S. Cl. ..................................... 549/416; 549/420
[58] Field of Search .................. 260/345.9 R, 345.7 R

[56] References Cited

U.S. PATENT DOCUMENTS 4,216,326  8/1980  Zenitz ................................. 546/226

*Primary Examiner*—Nicky Chan
*Attorney, Agent, or Firm*—Jacqueline S. Larson; Donald W. Erickson; Thomas T. Gordon

[57] ABSTRACT

The compound, cyclopropylmethyl 4-(2-cyclopropylcarbonyloxyethoxy)benzoate, novel intermediates therefor, synthesis thereof, and the use of said compound for the control of pests.

3 Claims, No Drawings

SUBSTITUTED PHENOXYETHOXYTETRAHYDROPYRAN

This is a division of application Ser. No. 166,649, filed July 7, 1980, now U.S. Pat. No. 4,304,924.

This invention relates to the novel compound, cyclopropylmethyl 4-(2-cyclopropylcarbonyloxyethoxy)-benzoate, novel intermediates therefor, synthesis thereof, and the use of said compound for the control of pests.

Cyclopropylmethyl 4-(2-cyclopropylcarbonyloxyethoxy)benzoate can be synthesized as outlined below:

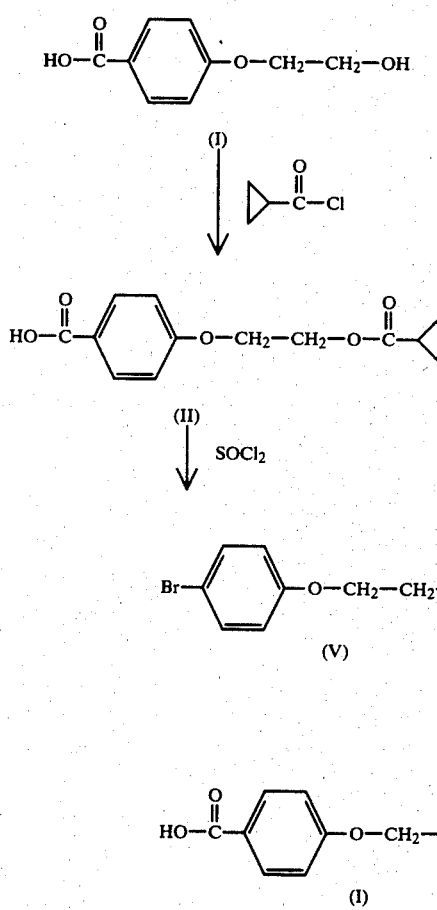

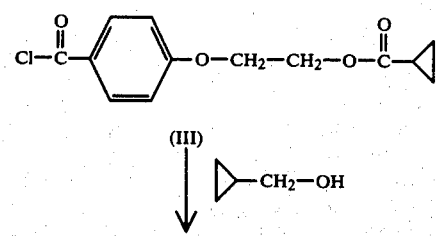

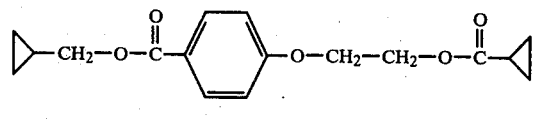

(IV)

In the practice of the above-outlined synthesis, 4-(hydroxyethoxy)benzoic acid (I) is esterified with cyclopropylcarboxylic acid chloride in the presence of pyridine and tetrahydrofuran. The resulting 4-(2-cyclopropylcarbonyloxyethoxy)benzoic acid (II) is halogenated by reaction with thionyl chloride in the presence of ether and dimethylformamide to give 4-(2-cyclopropylcarbonyloxyethoxy)benzoic acid chloride (III), which is converted to the final product, cyclopropylmethyl 4-(2-cyclopropylcarbonyloxyethoxy)benzoate (IV), by reaction with cyclopropylmethanol in the presence of pyridine.

The starting benzoic acid (I) is made by the reaction of 2-(4-bromophenoxy)ethanol (V) with dihydropyran, in the presence of methylene chloride and p-toluenesulfonic acid.$H_2O$, to give 4-(2-tetrahydropyranyloxyethoxy)bromobenzene (VI). The bromobenzene (VI) is converted to 4-(2-tetrahydropyranyloxyethoxy)benzoic acid (VII) by reacting with magnesium, in tetrahydrofuran and dibromoethane, and then with carbon dioxide. Reaction of (VII) with methanol yields the starting benzoic acid (I).

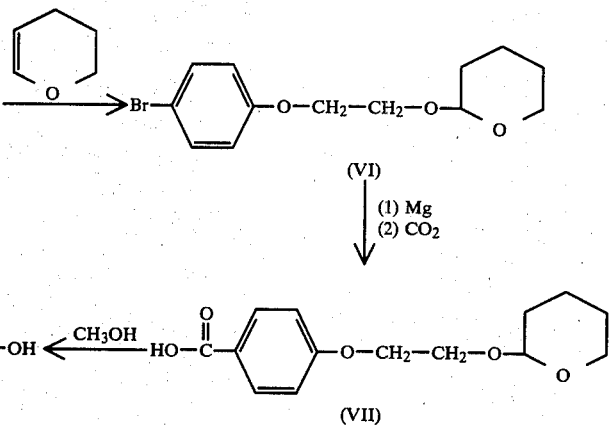

Cyclopropylmethyl 4-(2-cyclopropylcarbonyloxyethoxy)benzoate is an effective pesticide, particularly against insects and acarids. Without intention of being bound by theory, the compound appears to exhibit both activity associated with a standard insecticide, most notably as but not limited to an ovicide, and activity as an insect growth regulator, inhibiting metamorphosis and otherwise causing abnormal development of the insect. In the use of this compound for combating insects and acarids, the compound together with a carrier is applied to the locus in a pesticidally effective amount, generally at low dosage levels of the order of 0.0001 μg to 25 μg per animal. The carrier can be liquid or solid and include adjuvants such as wetting agents, dispersing agents and other surface active agents. Cyclopropylmethyl 4-(2-cyclopropylcarbonyloxyethoxy)benzoate can be used in formulations such as wettable powders, solutions, dusts, granules, emulsifiable concentrates, and the like. Suitable solid carriers include natural and synthetic silicates and clays, carbon or charcoal granules, natural and synthetic resins, waxes, and the like. Suitable liquid carriers include water, aromatic hydrocarbons, alcohols, vegetable and mineral oils, ketones, and the like. The amount of the compound of this invention in the formulation can vary widely, generally within the range of about 0.01 percent to about 90.0 percent, by weight.

The compound of the present invention is effective on many different insects and on acarids. The compound is an effective control agent for insects such as those of the order Lepidoptera, Orthoptera, Homoptera, Diptera, Coleoptera or Hymenoptera, and for acarids of the order Acarina including mites of the family Tetranychidae or Tarsonemidae.

The compound of the present invention can be used in combination with insect attractants and/or with other pesticides such as the carbamates, phosphates and insect growth regulators, e.g. propoxur, carbaryl, naled, dichlorvos, methoprene, kinoprene, hydroprene, cyhexatin and resmethrin.

The following examples are provided to illustrate the practice of the present invention. Temperature is given in degrees Centigrade. RT means room temperature. X means times.

EXAMPLE 1

To a mixture of 12.0 g (55.4 mmol) 2-(4-bromophenoxy)ethanol, 100 ml dry methylene chloride and 5.1 g (60.9 mmol) dihydropyran is added, at RT, 0.42 g (2.2 mmol) p-toluenesulfonic acid.water. The mixture is stirred for 3 days at RT, after which 50 ml methylene chloride, 50 ml water and 10 ml aqueous 15% potassium carbonate are added. The organic phase is separated and washed with water (60 ml) and with saturated aqueous sodium chloride, and is then dried over calcium sulfate. Solvent is removed by rotary evaporation to yield 4-(2-tetrahydropyranyloxyethoxy)bromobenzene.

A mixture of 9.45 g (31.4 mmol) of 4-(2-tetrahydropyranyloxyethoxy)bromobenzene, 40 ml of dry tetrahydrofuran (THF) and 0.76 g (31.4 mmol) of magnesium metal is heated to boiling, and after about 15 minutes a spontaneous reaction ensues. The mixture is then maintained, with some external heating, at its boiling point and after 15 minutes 20 ml of THF is added. After an additional 15 minutes at boiling, a final 20 ml of THF is added, and boiling is continued until the total heating time is 2 hours. Most of the magnesium has disappeared at this point. The mixture is then cooled and carbon dioxide gas is introduced, at a slight positive pressure and with vigorous stirring, for 15 minutes. The mixture is filtered and rotoevaporated to remove the solvent. Ethyl acetate (150 ml), water (150 ml) and aqueous 3 N sulfuric acid (20 ml) are added to the residue. The aqueous layer is separated and extracted with ethyl acetate. The combined organic layers are washed with water (100 ml, 2X) and then with saturated aqueous sodium chloride and dried over calcium sulfate. Solvent is removed by rotoevaporation to give 4-(2-tetrahydropyranyloxyethoxy)benzoic acid.

EXAMPLE 2

To a mixture of 7.7 g (37.7 mmol) of 4-(2-tetrahydropyranyloxyethoxy)benzoic acid and 31 ml (754 mmol) of anhydrous methanol, at RT, is added 2 drops of conc. sulfuric acid. The mixture is stirred at RT for 1 day and is then rotoevaporated to near dryness. To the residue is added 100 ml water, 50 ml ether and 30 ml aqueous 15% potassium carbonate, and the mixture is stirred until the solid is dissolved. The organic phase is separated and discarded; 150 ml of ethyl acetate and 50 ml of aqueous 3 N sulfuric acid are added to the remaining aqueous phase. The aqueous phase is then separated and extracted with ethyl acetate (80 ml, 3X). The combined organic phases are washed with aqueous saturated sodium chloride (50 ml, 2X) and then dried over calcium sulfate. Removal of solvent by rotoevaporation gives 4-(hydroxyethoxy)benzoic acid.

To 3.7 g (20.3 mmol) of 4-(hydroxyethoxy)benzoic acid, 100 ml of dry THF and 5.3 g (50.75 mmol) of cyclopropylcarboxylic acid chloride, at 0°, is added 6.6 ml (81.2 mmol) of pyridine. The mixture is allowed to warm to RT and is stirred at RT for 6 days, after which it is filtered. The filtrate is stirred, at RT, with 0.7 ml (~40.6 mmol) of water for 6 days. Solvent is removed by rotoevaporation, and 150 ml of ethyl acetate, 150 ml of water and 40 ml of aqueous 3 N sulfuric acid are added to the residue. The aqueous layer is separated and extracted once with 50 ml of ethyl acetate. The combined organic layers are washed with water (100 ml), with aqueous saturated cupric sulfate (50 ml), again with water (100 ml) and with aqueous saturated sodium chloride (50 ml) and are then dried over calcium sulfate. Solvent is removed by rotoevaporation, and the crude product is washed with 20 ml hexane (3X) and dried to yield 4-(2-cyclopropylcarbonyloxyethoxy)benzoic acid.

EXAMPLE 3

To a mixture of 3.2 g (12.8 mmol) of 4-(2-cyclopropylcarbonyloxyethoxy)benzoic acid, 80 ml of ether and 1.5 ml (20.5 mmol) of thionyl chloride, at RT, is added 0.3 ml (3.8 mmol) of dimethylformamide. This mixture is stirred, at RT, for 1 day. The top phase is decanted (the residue is discarded), and solvent and ohter volatiles are removed from it by rotoevaporation to give 4-(2-cyclopropylcarbonyloxyethoxy)benzoic acid chloride.

EXAMPLE 4

Ether (80 ml) and cyclopropylmethanol (1.5 g, 20.5 ml) are added to the 4-(2-cyclopropylcarbonyloxyethoxy)benzoic acid chloride obtained in Example 3, followed by the addition, at 0°, of 3.1 ml (38.4 mmol) of pyridine. The mixture is allowed to warm to RT and is stirred, at RT, for 1 day. Ether (60 ml), pentane (60 ml) and water (100 ml) are then added and the mixture is acidified with aqueous 3 N sulfuric acid. The organic layer is separated and is successively washed with aqueous 15% potassium carbonate (50 ml), water (50 ml, 2X), aqueous saturated cupric sulfate (40 ml), water (50 ml), and aqueous saturated sodium chloride (50 ml), and is then dried over calcium sulfate. Solvent removal by rotoevaporation yields the crude product, which is purified by distillation. The second fraction obtained is cyclopropylmethyl 4-(2-cyclopropylcarbonyloxyethoxy)benzoate, m.p. 43°–46°.

EXAMPLE 5

0–24 Hour-old eggs of *Samia cynthia* are placed on black electrical tape, 15 eggs per tape, and the tape with eggs is placed in a plastic petri dish. Each egg is treated topically with 1 μl of the test compound in acetone at different dosage rates, 15 eggs per dose level. Fifteen eggs are treated identically with acetone as controls. The eggs are held at 28° and 16 hours photoperiod for ten days or until the controls have hatched (moisture is provided after seven days with a cotton ball saturated with water). Scoring is of the number of unhatched eggs calculated as a percentage of the total number treated and then corrected for any mortality in the control group using Abbott's formula. The toxicity is expressed as $LD_{50}$, which is the dosage, in μg per egg, required to prevent hatching of 50% of the test eggs. The compound cyclopropylmethyl 4-(2-cyclopropylcarbonyloxyethoxy)benzoate gives an $LD_{50}$ of less than 0.0005 μg/egg.

First instar larvae, 0-24 hours old, of *Heliothis virescens* are placed individually in glass test tubes on a meridic diet in which the test compound, at a particular dose level, has been admixed. Fifteen larvae are tested per dose level, and fifteen larvae are placed on the diet without the compound as a control. The assay is incubated at 28° and 16 hours photoperiod and runs until the larvae have pupated. Observations for insect growth regulator (IGR) activity, such as pigmentation changes and larval-pupal intermediates, are made throughout the assay. The effect of the compound is expressed as $EC_{50}$, which is the concentration, in ppm, required to show IGR activity in 50% of the insects tested. The $EC_{50}$ of cyclopropylmethyl 4-(2-cyclopropylcarbonyloxyethoxy)benzoate is less than 0.5 ppm.

Five lima bean discs, 10 mm in diameter, are infested with 0-24 hr old *Tetranychus urticae* eggs and are then dipped in acetone dilutions of the compound to be tested. Other infested discs are dipped in acetone alone as a control. The solvent is allowed to evaporate and the discs are glued to the surface of a plastic petri dish. The eggs are incubated for four days at 25° and 16 hours photoperiod. The percentage of eggs which fail to hatch is determined, and the effect is stated as $EC_{50}$ or the concentration required to prevent hatching of 50% of the eggs. Cyclopropylmethyl 4-(2-cyclopropylcarbonyloxyethoxy)benzoate gives an $EC_{50}$ of 25.0 ppm.

Ten 0-24 hr old pupae of *Galleria mellonella* (Linnaeus) are removed from their cocoons and treated ventrally at the junction of the wing tips with 1 μl of acetone dilutions of the test compound. Controls are treated with acetone alone. The pupae are incubated at 31° and 16 hours photoperiod until the controls have emerged, about 8-10 days. Scoring is made for IGR activity, in this case retention of pupal characteristics in the developing moths. The $ED_{50}$ of cyclopropylmethyl 4-(2-cyclopropylcarbonyloxyethoxy)benzoate in this test is less than 5.0 μg/pupa.

Five-day old *Tetranychus urticae* larvae, held within a 2.5×2.5 cm lanolin grid on the dorsal surface of a leaf of a 2.5-3 week old lima bean plant, are sprayed until just before run-off with a formulation of the test compound in 0.1% Tween 20 in water. Two plants are treated per dose level and a control is treated with 0.1% Tween 20 in water alone. The plants are maintained at 26° and 16 hr photoperiod for 72 hours after spraying, after which they are scored. The activity is determined as the number of dead larvae and nymphs calculated as a percentage of the total number of larvae and nymphs present, with correction for control mortality by use of Abbott's formula. The $LC_{50}$ of cyclopropylmethyl 4-(2-cyclopropylcarbonyloxyethoxy)benzoate in this assay is less than 0.05%.

What is claimed is:

1. A compound of the following formula:

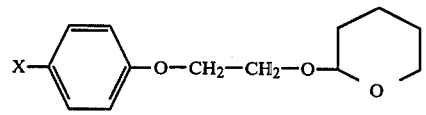

wherein, X is halogen or COOH.

2. The compound according to claim 1 wherein X is COOH.

3. The compound according to claim 1 wherein X is chloro or bromo.

* * * * *